United States Patent
Shimazu et al.

(10) Patent No.: US 6,995,107 B2
(45) Date of Patent: Feb. 7, 2006

(54) RANEY CATALYST, PROCESS FOR PRODUCING IT AND PROCESS FOR PRODUCING A SUGAR-ALCOHOL USING THE SAME

(75) Inventors: Koshiro Shimazu, Shizuoka (JP); Yoshiaki Tateno, Shizuoka (JP); Mitsuo Magara, Shizuoka (JP); Naoki Okamoto, Chiba (JP); Takao Ohshima, Saitama (JP); Minoru Nagasawa, Saitama (JP); Hideki Sakamura, Gunma (JP)

(73) Assignees: Towa Chemical Industry Co., Ltd., Tokyo (JP); Nikko Rica Corporation, Tokyo (JP)

( * ) Notice: Subject to any disclaimer, the term of this patent is extended or adjusted under 35 U.S.C. 154(b) by 10 days.

(21) Appl. No.: 10/997,952

(22) Filed: Nov. 29, 2004

(65) Prior Publication Data
US 2005/0153837 A1    Jul. 14, 2005

Related U.S. Application Data

(62) Division of application No. 09/197,499, filed on Nov. 23, 1998, now abandoned, which is a division of application No. 08/743,081, filed on Nov. 4, 1996, now Pat. No. 6,414,201.

(30) Foreign Application Priority Data

Nov. 8, 1995 (JP) .................................. 7-313720

(51) Int. Cl.
B01J 25/02 (2006.01)
C07C 31/26 (2006.01)

(52) U.S. Cl. .................. 502/25; 502/301; 568/863

(58) Field of Classification Search ............. 502/22, 502/24, 25, 301, 302, 346; 568/863, 861; 560/263; 252/466
See application file for complete search history.

(56) References Cited

U.S. PATENT DOCUMENTS

| | | | |
|---|---|---|---|
| 1,628,190 A | 10/1927 | Raney | 502/301 |
| 2,948,687 A | 8/1960 | Hadley | 502/315 |
| 3,165,478 A * | 1/1965 | Ulrich et al. | 502/28 |
| 3,673,116 A | 6/1972 | Richter | 252/466 |
| 3,719,732 A | 3/1973 | Diffenbach et al. | 264/9 |
| 4,166,805 A * | 9/1979 | Jowett | 502/167 |
| 4,258,222 A | 3/1981 | Mohring et al. | 568/863 |
| 4,263,449 A | 4/1981 | Saito et al. | 560/263 |
| 4,322,569 A | 3/1982 | Chao et al. | 568/863 |
| 4,520,211 A | 5/1985 | Lepper | 568/863 |
| 4,554,397 A | 11/1985 | Stern | 585/638 |
| 4,628,130 A | 12/1986 | Bournonville et al. | 568/885 |
| 4,826,799 A | 5/1989 | Cheng et al. | 502/301 |
| 5,093,528 A | 3/1992 | Dobson et al. | 564/472 |
| 5,362,519 A | 11/1994 | Argyropoulos et al. | 427/385.5 |
| 5,536,694 A | 7/1996 | Schuetz et al. | 502/301 |
| 5,641,872 A | 6/1997 | Darow | 568/863 |
| 5,873,943 A * | 2/1999 | Magara et al. | 127/29 |

OTHER PUBLICATIONS

Smarsh, Powder Coating: Why-How-When, Journal of Paint Technology, vol. 44, No. 565, p. 30-37, Feb., 1972.

* cited by examiner

Primary Examiner—Ngoc-Yen Nguyen
(74) Attorney, Agent, or Firm—Birch, Stewart, Kolasch & Birch, LLP

(57) ABSTRACT

To obtain a Raney catalyst for fixed bed permitting a continuous use with a high initial activity and to produce a high purity sugar-alcohol at a low cost using the same.

For this object, sugar-alcohol is produced by: using the powder type Raney catalyst made by using for the hydrogenation under the hydrogen pressure a lump form Raney catalyst made by (i) the first step for melting nickel and aluminum, (ii) the second step for obtaining quenched lump alloy by quenching droplets of said melted mixture and (iii) the third step for classifying and activating said quenched lump alloy as it is or once it is broken, collecting said lump form Raney catalyst, crushing into powder and reactivating, and hydrogenating sugars under the hydrogen pressure.

1 Claim, 1 Drawing Sheet

RANEY CATALYST, PROCESS FOR PRODUCING IT AND PROCESS FOR PRODUCING A SUGAR-ALCOHOL USING THE SAME

This application is a Divisional of parent application Ser. No. 09/197,499, which was filed on Nov. 23, 1998 abandoned, which is a Divisional of grandparent application Ser. No. 08/743,081, which was filed Nov. 4, 1996, and which issued as U.S. Pat. No. 6,414,201B1 on Jul. 2, 2002, and for which priority is claimed under 35 U.S.C. § 120; and this application claims priority of application Ser. No. 7-313,720 filed in Japan on Nov. 8, 1995 under 35 U.S.C. § 119; the entire contents of all are hereby incorporated by reference.

TECHNICAL FIELD

The present invention concerns a Raney catalyst for hydrogenation, a process for producing it and a process for producing the sugar-alcohol using the same.

BACKGROUND ART

Actual sugar-alcohols produced industrially include sorbitol, mannitol, maltitol, xylitol and others and they are used in quantity as food additives, industrial materials or pharmaceutical materials.

In general, these sugar-alcohols are produced by the heating reaction of sugars under the hydrogen pressure in the presence of a hydrogenation catalyst.

A supported ruthenium catalyst, a Raney catalyst or the like are known as the hydrogenation catalyst used for sugar-alcohol production.

Though the supported ruthenium catalyst presents a very high catalytic activity, it provokes inconveniently sugar isomerization, decomposition and polymerization during the hydrogenation.

For solving this inconvenience, the British patent No. 867,689 describes Ru—Pd catalyst carried by activated carbon wherein ruthenium is added to palladium, however, the purity of sorbitol produced by the patent remained between 93.5 and 97.5%.

On the other hand, the Japanese TOKKYO-KOKAI-KOHO (18-month Publication of Unexamined Patent Application) SHOWA (hereinafter referred to as TOKKAISHO) 51-4370 describes Ru catalyst carried by zeolite aluminosilicate while the Japanese TOKKAISHO 51-82208 describes an example of glucose hydrogenation by Ru catalyst carried by crystalline clay aluminosilicate, but their results were not satisfactory because the purity of sorbitol is not superior to 99% in either case.

Raney catalyst is a catalyst activated by dissolving a part of metals such as aluminum, zinc and silicon by an alkali from alloys of catalytic metals such as nickel, copper and iron and metals such as aluminum, zinc and silicon.

The catalyst presents in general a low catalytic activity and a high catalyst deterioration and the catalyst cost assumes disadvantageously a great part of the product price.

Moreover, as the catalyst is supplied mainly in powder form and used by batch method, it is necessary to provide a step for separating the catalyst from the reaction solution after the hydrogenation, the production cost increases as much.

In order to remedy this defect, a variety of Raney catalysts for fixed bed have been developed, none of them leading to a satisfactory solution.

For instance, the Japanese TOKKAISHO 50-099987 describes a method for producing a Raney catalyst for fixed bed based on nickel, cobalt or copper precipitation type catalyst.

In the method, conventional nickel, cobalt or copper precipitation type catalyst is blended and formed with powder metal/aluminum alloy and then treated at a high temperature using steam. During this step, $\gamma$-$Al_2O_3$ acting as binder is generated, but as the formed body is destroyed by the dissolution of $\gamma$-$Al_2O_3$ in the step of activation by an alkali, it is not appropriate for the production of Raney catalyst for fixed bed.

The Japanese TOKKAISHO 47-27888 describes a method for producing a Raney catalyst for fixed bed by dropping melted alloy in or on a chilled solvent to form a catalyst and activating it.

It is important to increase the density of catalyst to be loaded and to regulate the solution flow in the fixed bed for efficient hydrogenation during the sugar-alcohol production. For this sake, it is preferable to limit the catalyst grain diameter to 4 mm or less but, if the grain diameter is too small, the resistance increases and the solution flow slows down in a way to provoke obstruction of broken catalyst, so the preferable grain diameter is 2 to 4 mm approximately.

However, if it is desirable to obtain an uniform granulating in the catalyst production, the grain diameter of this range will only be obtained in the sacrifice of the yield by the method described in the Japanese TOKKAISHO 47-27888 wherein alloy grains are produced by dropping melted metal from an orifice. Additionally, alloy grains out of this diameter range should be melted again so as to increase the cost as much.

Theretofore, the object of the present invention is to obtain a Raney catalyst for fixed bed remedying various problems mentioned hereinbefore and to produce a high purity sugar-alcohol at a low cost using the same.

DISCLOSURE OF THIS INVENTION

Now the present invention will be described more in detail.

In the present invention, the nickel and aluminum ratio of quenched lump alloy may be adopted between the range of 1:2 to 2:1, however, the ratio approximately 1:1 is preferable considering the alloy cost and the catalyst activity after the development.

Droplets of melted alloy are quenched forcefully by dropping into a water bath or by another way. Raney catalyst produced by activating lump alloy obtained by chilling through natural radiation may provide an initial activity but the catalyst breaks down according to the increase of use time and can not be used as fixed bed catalyst.

Preferably, droplets of melted alloy are so made to obtain their grain diameter between 1 and 15 mm after the quench.

After classification and activation as it is, the quenched lump alloy may be used as fixed bed catalyst, however, in order to increase the catalyst surface area, it is preferable that the quenched lump alloy is classified after breaking, activated and then used as fixed bed catalyst.

Either when the quenched lump alloy as it is or after break is classified, if the grain diameter is too small, it is difficult to compose a fixed catalyst layer and even when it is composed, reaction mixture flows more slowly and it is no more possible to produce sugar-alcohol with a high productivity. On the other hand, if grains are too large, surface area per unit catalyst weight decreases so as to reduce the reaction speed and the productivity of sugar-alcohol.

To the lump form Raney catalyst according to the invention, is possible to add molybdenum, tin or the like up to 15% of catalyst metal in order to afford it with a function of its catalytic property or it is also possible to add after the activation of the catalyst.

Aqueous solution of NaOH, KOH or other alkali metal hydroxide may be used as alkali for the catalyst development and its concentration is 1 to 20%, preferably 5 to 15%. The development temperature is 40 to 100° C., preferably 60 to 85° C.

The development rate of the obtained catalyst may be determined by the following formulation after measuring the elution amount of aluminum into the alkali by means of chelatometric titration or the like.

Development rate (%)=(elution amount of aluminum/ amount of aluminum in the alloy)×100

The development rate of the lump form Raney catalyst according to the invention is 10 to 70%, preferably 15 to 60%.

The development rate is closely related to the catalyst life and the catalyst cost assumed in the sugar-alcohol production is determined by the catalyst life. The catalyst life varies according to alloy composition, kind of sugar-alcohol to be produced or others but it should assure a continuous operation.

For this sake, it is developed within the range of 10 to 70%. If the development rate is less than 10%, the expected initial activity can not be obtained and if it is higher than 70%, high initial activity is obtained but the catalyst life is shortened. This is because the catalyst becomes fragile and nickel peels off in fine powder.

The hydrogen used in the conduction of the process for producing the sugar-alcohol using the Raney catalyst according to the invention is not limited particularly, but higher purity is more preferable.

Sugars that may be hydrogenated in the invention include glucose, xylose, maltose, lactose, fructose, starch saccharificate, sucrose or the like. They can be used alone or in combination of more than one kinds.

Normally, these sugars are supplied to the fixed bed as aqueous solution within the concentration range of 30 to 60%. If the concentration is low, the productivity will be low and if it is high, it will be difficult to eliminate reaction heat so as to deteriorate the purity of sugar-alcohol.

Material sugar is normally supplied to the fixed bed within the range of SV=0.3 to 1.5.

Here, SV is determined according to the following formulation.

SV=(Material volume supplied into the reactor)/(Volume occupied by catalyst loaded into the reactor)

Hydrogen flow rate supplied to the fixed bed is, normally, LV=10 to 60 m/hr and preferably LV=15 to 30 m/hr.

Here, LV can be determined by the following formulation:

LV=(Substance volume supplied into the reactor per unit time)/(Sectional area of the reactor)

The reaction temperature for the conduction of the process for producing the sugar-alcohol using the Raney catalyst according to the invention varies depending on sugar-alcohols to be produced but is 110 to 150° C. and preferably 120 to 145° C. The hydrogen pressure is, normally, about 40 to 200 Kg/cm$^2$ and preferably 50 to 150 Kg/cm$^2$.

The reaction form using the lump form Raney catalyst according to the invention corresponds to the continuous reaction on the fixed bed including an upflow method wherein sugar solution is supplied from the bottom of the reactor and a downflow method wherein the same flows down from the top of the reactor and the both may be adopted equally.

The reactor shape used for this reaction may be either bath, tubular or tower type.

When the upflow method is adopted, LV of the solution flowing inside should be at least 1 m/hr and preferably 4 to 8 m/hr. LV of hydrogen is 10 to 60 m/hr and preferably 15 to 30 m/hr.

When the downflow method is adopted, as the hydrogen occupies more space in the reactor, the hydrogen flow might be less and the hydrogen LV is conducted within the range of 1 to 10 m/hr.

After being used for the hydrogenation of sugar under the hydrogen pressure, the lump form Raney catalyst according to the invention is collected, crushed into powder and reactivated to be reused as powder form Raney catalyst. Hence, when the present invention is conducted, me total catalyst cost may be reduced to a level lower than when the conventional powder Raney nickel catalyst is used.

The method for crushing into powder for the collected lump form Raney catalyst is not particularly limited if only powder Raney catalyst of the granuometry appropriate for the use can be obtained finally. In general, it is crushed into within the particle size of total pass through 40 mesh, preferably within the particle size of total pass through 300 mesh.

The development of powder Raney catalyst at the reactivation is conducted at the development rate of 90 to 97% under the usual conditions.

Any reaction conditions may be applied for the preparation of sugar-alcohol by the hydrogenation with the presence of powder Raney catalyst only if the purity of sugar-alcohol is not deteriorated, however, normally, the reaction is conducted with the sugar concentration of 30 to 60%, under the hydrogen pressure of at least 40 Kg/cm$^2$, preferably 50 to 150 Kg/cm$^2$ and at the temperature of 110 to 150° C.

The Raney catalyst according to the invention is a catalyst for fixed bed permitting a continuous use with a high initial activity by quenching melted alloy.

According to the process for producing the Raney catalyst of the invention, Raney catalyst, which is fixed bed catalyst, may be obtained through a short production process, without using binder for shaping, moreover, the production of the catalyst requires no special equipment.

Additionally, used lump form Raney catalyst may be collected, crushed into powder and then reactivated to be reused.

Thus, the process for producing the sugar-alcohol using Raney catalyst according to the invention allows to produce a high purity sugar-alcohol at a low cost.

Figure 1:
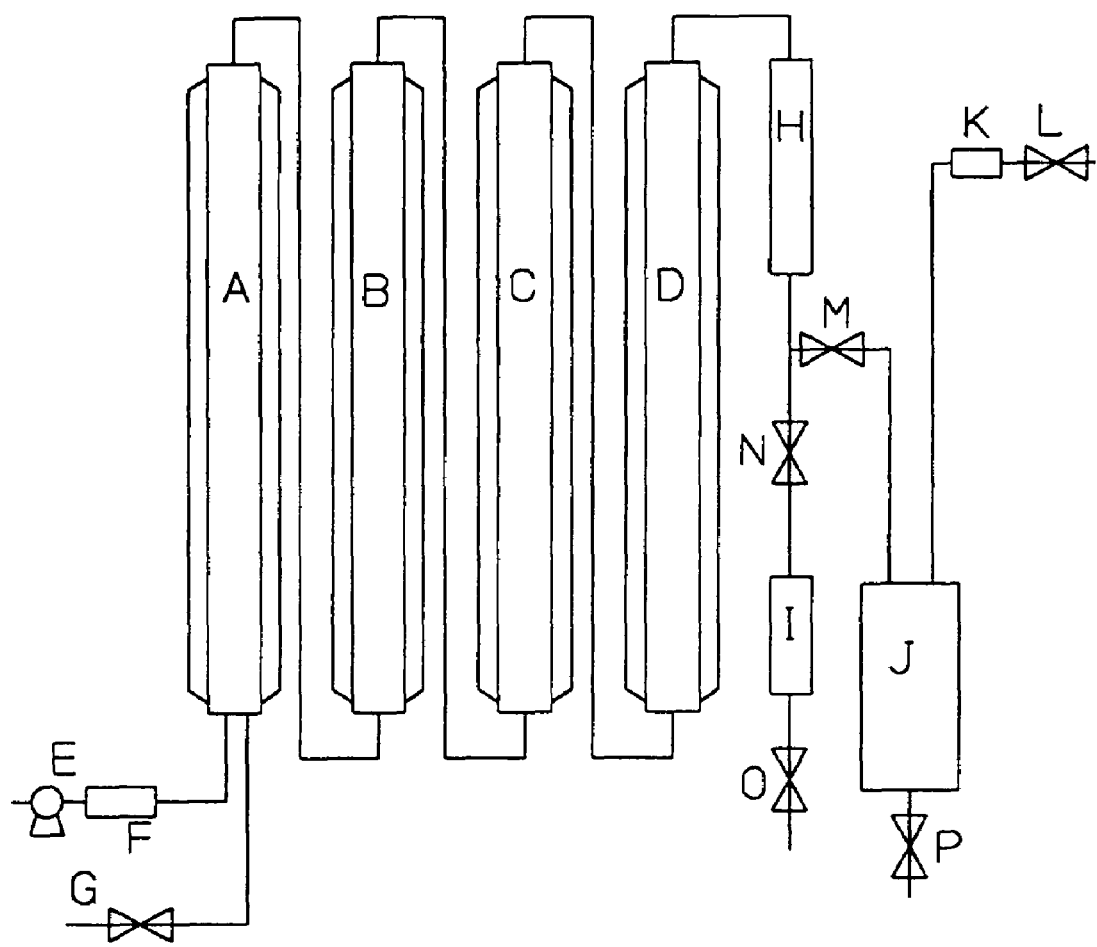
FIG. 1 is a schematic view of a hydrogenation equipment used for the conduction of the process for producing the sugar-alcohol using Raney catalyst according to the invention.

In this drawing, A refers to tower, F preheater, H refrigerator and J solution reservoir pot.

DESCRIPTION OF PREFERRED EXAMPLES

Now the present invention will be described more in detail referring to Examples or Reference Examples which do not limit the technical scope of the invention.

Example 1

[Production of Quenched Lump Alloy]

6 Kg of nickel metal and 6 Kg of aluminum metal were heat-melted and dropped onto chilled water surface 20 cm below through a nozzle.

The grain diameter of the obtained quenched lump alloy was a mixture of 1 mm to 15 mm.

It was broken by a crusher and meshed to obtain 4.98 Kg of quenched lump alloy of grain diameter 2 to 4 mm.

[Development of quenched Lump Alloy]

34 Kg of 10% NaOH aqueous solution was poured into a 50 liter stainless container provided with heating jacket, heated to 50° C. and 4.6 Kg of the quenched lump alloy contained in a stainless cage was put therein.

It was held at 60° C. for 30 minutes and then the cage was lifted up and washed with water.

The development rate of lump form Raney catalyst thus obtained was 21.6%.

[Hydrogenation Equipment]

Now the hydrogenation equipment used for the conduction of the process for producing the sugar-alcohol using Raney catalyst according to the invention will be described referring to FIG. 1.

The hydrogenation equipment comprises four (4) stainless pressure vessels (inner diameter 2.1 cm, height 160 cm) of 0.5 liter with jacket connected in series and represented by A, B, C and D in the drawing, wherein a material feeding pump E is connected to the bottom of the tower A via a pre-heater F, a sampling pot I and a solution reservoir pot J are respectively connected to the top of the tower D via a refrigerator H.

Hydrogen gas enters into the bottom of the tower A, exits from the top of the tower D, is separated from solution in the solution reservoir pot J and is blown into the air through a flow meter K and regulator L.

Heated oil flows through the pre-heater F and the jacket of towers A, B, C and D to keep the temperature constant.

Normally, a valve M is open and valves N, O and P are closed and the reaction solution coming from the tower D is reserved in the pot J and discharged from a valve P from time to time.

For sampling, the valve M is closed and the valve N is opened to discharge sample from the pot I through the valve O.

[Hydrogenation Reaction]

Developed lump form Raney catalyst was loaded into the reactor.

Then, respective towers were heated to 130° C. and aqueous-solution of 50% crystalline glucose (purity 99.7%, made by Nihon Shokuhin Kako Co., Ltd.) was supplied from the pump E at the flow rate of 2 liter/hr (SV=1).

Hydrogen was adjusted to LV=20 at 150 Kg/cm$^2$.

Hydrogenation reaction was operated continuously for 30 days and nonreducing substance in the reaction solution and purity measurement results by liquid chromatography of this period are shown in the Table 1.

TABLE 1

| Reaction time | Nonreducing substance (%) | Sorbitol purity (%) |
|---|---|---|
| First Day | 0.07 | 99.3 |
| 5th Day | 0.10 | 99.2 |
| 10th Day | 0.14 | 99.2 |

TABLE 1-continued

| Reaction time | Nonreducing substance (%) | Sorbitol purity (%) |
|---|---|---|
| 20th Day | 0.23 | 99.1 |
| 30th Day | 0.32 | 99.0 |

[Catalyst Reuse]

After the hydrogenation reaction of 30 days, catalyst was washed with water, unloaded from respective towers and 50 g of collected catalyst was crushed in the water by a crusher up to total pass through 100 mesh.

Then, 400 g of 20% NaOH aqueous solution was added, stirred for one hour at 95° C. and then washed with water to obtain powder Raney catalyst.

5 g (as dry solid) of thus obtained powder Raney catalyst and 275 g of 50% crystalline glucose aqueous solution were put into an electromagnetic stirring type autoclave of 550 ml and stirred at 130° C. for 90 minutes under the hydrogen pressure of 150 Kg/cm$^2$.

At this time, the nonreducing substance in the reaction solution was 0.08%.

For reference, the nonreducing substance in the reaction solution was 0.07% when crystalline glucose was hydrogenated under the same condition using 5 g of commercially available powder Raney nickel catalyst and no difference of catalytic activity was observed in comparison with the reuse of powder Raney catalyst obtained from the used lump form Raney catalyst.

Example 2

The reaction was conducted in a similar way to the Example 1 except that 50% crystalline glucose aqueous solution was supplied as raw material at the rate of 1 liter per hour (SV=0.5) and the continuous hydrogenation was proceeded for 3 days.

The analysis results of the obtained reaction solution are shown in the Table 2.

TABLE 2

| Reaction time | Nonreducing substance (%) | Sorbitol purity (%) |
|---|---|---|
| First Day | 0.02 | 99.2 |
| Third Day | 0.03 | 99.2 |

Example 3

The reaction was conducted in a similar way to the Example 1 except that 50% xylose aqueous solution (purity 99.0%) was supplied as raw material at the rate of 1.4 liter per hour (SV=0.7) and the continuous hydrogenation was proceeded for 5 days at 120° C.

The analysis results of the obtained reaction solution are shown in the Table 3.

As the results show, the catalyst prepared by the method of the Example 1 was able to be used satisfactorily for the hydrogenation of xylose.

TABLE 3

| Reaction time | Nonreducing substance (%) | Xylitol purity (%) |
|---|---|---|
| First Day | 0.05 | 98.4 |
| Third Day | 0.09 | 98.2 |
| 5th Day | 0.17 | 98.1 |

Example 4

The reaction was conducted in a similar way to the Example 1 except that 50% maltose aqueous solution (purity 95.2%, made by Nihon Shokuhin Kako Co., Ltd.) as raw material was supplied at the rate of 1.2 liter per hour (SV=0.6) and the continuous hydrogenation was proceeded for 5 days at 135° C.

The analysis results of the obtained reaction solution are shown in the Table 4.

As the results show, a constant purity maltitol has been produced for 5 days continuous hydrogenation without remarkable increase of nonreducing substance.

TABLE 4

| Reaction time | Nonreducing substance (%) | Maltitol purity (%) |
| --- | --- | --- |
| First Day | 0.04 | 94.9 |
| Third Day | 0.06 | 94.9 |
| 5th Day | 0.07 | 94.9 |

Example 5

The reaction was conducted in a similar way to the Example 1 except that 50% aqueous solution of starch hydrolysate (TN-55, made by Japan Corn Starch Co., Ltd.) as raw material was supplied at the rate of 1.4 liter per hour (SV=0.7) and the continuous hydrogenation was proceeded for 5 days at 145° C.

The composition of the used starch hydrolysate was glucose 2.2%, maltose 53.6%, maltotriose 19.1%, tetrasaccharide or more 25.1%.

The analysis results of the obtained reaction solution are shown in the Table 5.

Using the catalyst prepared acceding to the method of the Example 1, even raw material containing much component of relatively high molecular weight such as trisaccharide or more could be hydrogenated continuously.

TABLE 5

| | Reaction time | | |
| --- | --- | --- | --- |
| | First Day | Third Day | 5th Day |
| Nonreducing substance (%) | 0.09 | 0.13 | 0.18 |
| Sugar-alcohol composition of reaction solution (%) | | | |
| Sorbitol | 2.2 | 2.3 | 2.2 |
| Maltitol | 54.2 | 54.0 | 53.8 |
| Maltotriitol | 18.4 | 18.7 | 18.9 |
| Hydrogenated tetrasuccharide or more | 25.1 | 25.0 | 25.1 |

Example 6

The reaction was conducted in a similar way to the Example 1 except that 40% lactose aqueous solution as raw material was supplied at the rate of 1.6 liter per hour (SV=0.8) and the continuous hydrogenation was proceeded for 3 days at 140° C.

The analysis results of the obtained reaction solution are shown in the Table 6.

TABLE 6

| Reaction time | Nonreducing substance (%) | Lactitol purity (%) |
| --- | --- | --- |
| First Day | 0.03 | 99.2 |
| Third Day | 0.04 | 99.2 |

Example 7

The reaction was conducted in a similar way to the Example 1 except that 40% crystalline fructose aqueous solution as raw material was supplied at the rate of 1.6 liter per hour (SV=0.8) and the continuous hydrogenation was proceeded for 3 days at 125° C.

The analysis results of the obtained reaction solution are shown in the Table 7.

TABLE 7

| | Reaction time | |
| --- | --- | --- |
| | First Day | Third Day |
| Nonreducing substance (%) | 0.05 | 0.07 |
| Sorbitol (%) | 51.4 | 51.3 |
| Mannitol (%) | 48.2 | 48.3 |
| Others (%) | 0.4 | 0.4 |

Example 8

The reaction was conducted in a similar way to the Example 1 except that 50% sugar aqueous solution as raw material was supplied at the rate of 2.4 liter per hour (SV=1.2) and the continuous hydrogenation was proceeded for 3 days at 160° C.

The analysis results of the obtained reaction solution are shown in the Table 8.

TABLE 8

| | Reaction time | |
| --- | --- | --- |
| | First Day | Third Day |
| Nonreducing substance (%) | 0.04 | 0.05 |
| Sorbitol (%) | 75.0 | 75.0 |
| Mannitol (%) | 24.2 | 24.3 |
| Others (%) | 0.8 | 0.7 |

Example 9

[Hydrogenation Equipment]

The hydrogenation equipment used for this Example is not illustrated but it concerns an equipment similar to the hydrogenation equipment of FIG. 1, wherein the raw material feeding pump E is connected to the top of the tower A through the pre-heater F, the sampling pot I and the solution reservoir pot J are respectively connected to the bottom of the tower D through the refrigerator H.

In the equipment, the bottom of the tower A was connected to the top of the tower B, the bottom of the tower B to the top of the tower C and the bottom of the tower C to the top of the tower D respectively.

Thus, the hydrogenation equipment used for this Example is similar to the hydrogenation equipment of the Example 1 shown in FIG. 1 except that the hydrogen gas enters into the top of the tower A and exits from the bottom of the tower D.

Hydrogenation Reaction

In the Example 1, the reaction was conducted in a similar way to the Example 1 except that 50% crystalline glucose aqueous solution as raw material was supplied at the rate of 1 liter per hour (SV=0.5) and the continuous hydrogenation was proceeded with the hydrogen flow rate of 2 liters per hour.

The analysis results of the obtained reaction solution are shown in the Table 9.

TABLE 9

| Reaction time | Nonreducing substance (%) | Sorbitol purity (%) |
|---|---|---|
| First Day | 0.07 | 99.3 |
| 5ht Day | 0.09 | 99.3 |
| 10th Day | 0.11 | 99.1 |

Example 10

34 Kg of 10% NaOH aqueous solution was poured into a 50 liter stainless container provided with heating jacket and heated to 60° C.

4.6 Kg of quenched lump alloy of grain diameter 2 to 4 mm produced in a way similar to the Example 1 and contained in a stainless cage was put into the said aqueous solution of NaOH.

It was held at 80° C. for 2 hours and then the cage was lifted up and washed with water.

Here, the catalyst development rate was 40.8%.

This catalyst was loaded into an equipment similar to the one of the Example 1 and crystalline glucose was hydrogenated under the similar hydrogenation conditions.

The analysis results thereof are shown in the Table 10.

Compared to the Example 1, glucose could be hydrogenated continuously for a long time even when the catalyst development rate was increased to 40.8%.

Moreover, the destruction of catalyst was not observed.

TABLE 10

| Reaction time | Nonreducing substance (%) | Sorbitol purity (%) |
|---|---|---|
| First Day | 0.05 | 99.3 |
| 5th Day | 0.08 | 99.3 |
| 10th Day | 0.18 | 99.1 |
| 20th Day | 0.46 | 98.8 |
| 30th Day | 0.72 | 98.7 |

Example 11

55 Kg of 15% NaOH aqueous solution was poured into a 50 liter stainless container provided with heating jacket and heated to 60° C.

4.6 Kg of quenched lump alloy of grain diameter 2 to 4 mm produced in a way similar to the Example 1 and contained in a stainless cage was put into the said aqueous solution of NaOH.

It was held at 80° C. for 2.5 hours and then the cage was lifted up and washed with water.

Here, the catalyst development rate was 58.9%.

This catalyst was loaded into an equipment similar to the one of the Example 1 and crystalline glucose was hydrogenated under the similar hydrogenation conditions.

The analysis results thereof are shown in the Table 11.

Compared to the Example 1, if the catalyst development rate was increased to 58.9%, the catalyst activity decreased rather rapidly during the continuous operation but within a satisfactory range from the view point of industrial used because it did not provoke the destruction of catalyst.

TABLE 11

| Reaction time | Nonreducing substance (%) | Sorbitol purity (%) |
|---|---|---|
| First Day | 0.05 | 99.3 |
| 5th Day | 0.26 | 99.1 |
| 10th Day | 0.48 | 98.7 |
| 20th Day | 1.20 | 98.1 |

Example 12

25 Kg of nickel metal and 25 Kg of aluminum metal were heat-melted and dropped onto chilled water surface 20 cm below through a nozzle.

The grain diameter of thus obtained quenched lump alloy was within the range of 1 to 15 mm. It was screened by a sieve to obtain 6.2 Kg of quenched lump alloy of grain diameter 2 to 4 mm.

34 Kg of 10% NaOH aqueous solution was poured into a 50 liter stainless container provided with heating jacket, heated to 60° C. and 4.6 Kg of the quenched lump alloy contained in a stainless cage was put therein.

It was held at 80° C. for 25 minutes and then the cage was lifted up and washed with water.

The development rate of catalyst thus obtained was 22.4%.

The reaction was conducted in similar hydrogenation conditions to the Example 1 except that the obtained lump form Raney catalyst was loaded into the same equipment as the Example 1 and 50% glucose was supplied at the rate of 1.2 liter per hour (SV=0.6).

The analysis results thereof are shown in the Table 12.

As the results show, the quenched lump form catalyst of the invention could hydrogenate sugars even when it was activated as it is without break.

Then, after a continuous operation of 30 days, the catalyst was collected, powdered and developed in a similar way to the Example 1 before hydrogenating crystalline glucose once more.

Here, the nonreducing substance was 0.08% and the catalyst activity was within the satisfactory range.

TABLE 12

| Reaction time | Nonreducing substance (%) | Sorbitol purity (%) |
|---|---|---|
| First Day | 0.06 | 99.1 |
| 5th Day | 0.09 | 99.1 |
| 10th Day | 0.12 | 99.1 |
| 20th Day | 0.26 | 98.8 |
| 30th Day | 0.38 | 98.7 |

Example 13

Quenched lump alloy obtained in the Example 12 was screened by a sieve to obtain 8.6 Kg of quenched lump alloy of grain diameter 4 to 8 mm.

34 Kg of 10% NaOH aqueous solution was poured into a 50 liter stainless container provided with heating jacket, heated to 60° C. and 4.6 Kg of said quenched lump alloy contained in a stainless cage was put therein.

It was held at 80° C. for 120 minutes and then the cage was lifted up and washed with water.

The development rate of catalyst thus obtained was 38.6%.

The hydrogenation was conducted in similar conditions to the Example 1 except that this catalyst was loaded into the same equipment as the Example 1 and 50% glucose was supplied at the rate of 0.8 liter per hour (SV=0.4).

The analysis results thereof are shown in the Table 13.

The catalyst activity was satisfactory even when the grain diameter of catalyst was prepared to 4 to 8 mm.

TABLE 13

| Reaction time | Nonreducing substance (%) | Sorbitol purity (%) |
| --- | --- | --- |
| First Day | 0.06 | 99.0 |
| 5th Day | 0.10 | 99.0 |
| 10th Day | 0.15 | 98.9 |
| 20th Day | 0.32 | 98.7 |
| 30th Day | 0.64 | 98.5 |

Reference Example 1

6 Kg of nickel metal and 6 Kg of aluminum metal were heat-melted, poured onto a metal plate and left there.

The obtained alloy was broken by a crusher and screened through a sieve to obtain 5.3 Kg of alloy within the grain diameter range of 2 to 4 mm.

34 Kg of 10% NaOH aqueous solution was poured into a 50 liter stainless container provided with heating jacket and heated to 60° C.

4.6 Kg of the alloy contained in a stainless cage was put into the said NaOH aqueous solution. It was held at 60° C. for 30 minutes and then the cage was lifted up and washed with water.

The development rate of catalyst thus obtained was 23.8%.

Crystalline glucose was hydrogenated under the similar conditions as the Example 1 except that this catalyst was used, however, the reaction was suspended as the nonreducing substance increased suddenly at the 5th day.

Moreover, broken powder catalyst was observed in the reaction solution.

The analysis results of this are shown in the Table 14.

TABLE 14

| Reaction time | Nonreducing substance (%) | Sorbitol purity (%) |
| --- | --- | --- |
| First Day | 0.56 | 98.8 |
| 5th Day | 1.26 | 98.2 |

Reference Example 2

55 Kg of 15% NaOH aqueous solution was poured into a 50 liter stainless container provided with heating jacket and heated to 60° C.

4.6 Kg of quenched lump alloy made by the same method as the Example 1 and contained in a stainless cage was put into the NaOH aqueous solution.

It was held at 80° C. for 4 hours and then the cage was lifted up and washed with water.

The development rate of catalyst thus obtained was 73.8%.

Crystalline glucose was hydrogenated by the same method as the Example 1 except that this catalyst was used; when the solution has been supplied for 10 days, the reaction was suspended as broken catalyst obstructed the equipment.

The analysis results of this are shown in the Table 15.

TABLE 15

| Reaction time | Nonreducing substance (%) | Sorbitol purity (%) |
| --- | --- | --- |
| First Day | 0.05 | 99.3 |
| 5th Day | 0.18 | 99.2 |
| 10th Day | 0.86 | 98.7 |

What is claimed is:

1. A process for producing a powder Raney catalyst comprising:
   (i) melting nickel and aluminum,
   (ii) quenching droplets of said melted mixture by means of dropping them onto chilled water through a nozzle to obtain a quenched lump alloy,
   (iii) optionally breaking the quenched lump alloy,
   (iv) classifying and activating the alloy of step (ii) or (iii),
   (v) using said alloy of step (iv) as a Raney catalyst in a hydrogenation reaction,
   (vi) collecting said alloy of step (v),
   (vii) crushing said Raney catalyst used in the hydrogenation reaction into powder, and
   (viii) reactivating.

* * * * *